US007008424B2

(12) United States Patent
Teitelbaum

(10) Patent No.: US 7,008,424 B2
(45) Date of Patent: Mar. 7, 2006

(54) PERCUTANEOUS VERTEBRAL FUSION SYSTEM

(75) Inventor: George P. Teitelbaum, Santa Monica, CA (US)

(73) Assignee: University of Southern California, Los Angeles, CA (US)

(*) Notice: Subject to any disclaimer, the term of this patent is extended or adjusted under 35 U.S.C. 154(b) by 0 days.

(21) Appl. No.: 10/688,646

(22) Filed: Oct. 17, 2003

(65) Prior Publication Data

US 2004/0087950 A1    May 6, 2004

Related U.S. Application Data

(62) Division of application No. 09/747,066, filed on Dec. 21, 2000, now Pat. No. 6,821,277.

(60) Provisional application No. 60/213,385, filed on Jun. 23, 2000.

(51) Int. Cl.
*A56B 17/58*    (2006.01)
(52) U.S. Cl. ...................................................... 606/61
(58) Field of Classification Search ........... 604/103.06, 604/103.08, 103.09; 606/195, 92–94, 61
See application file for complete search history.

(56) References Cited

U.S. PATENT DOCUMENTS

| | | | |
|---|---|---|---|
| 2,267,925 A | | 12/1941 | Johnston |
| 3,834,394 A | * | 9/1974 | Hunter et al. ............... 606/195 |
| 3,875,595 A | | 4/1975 | Froning |
| 4,041,939 A | | 8/1977 | Hall |
| 4,289,123 A | | 9/1981 | Dunn |
| 4,327,734 A | | 5/1982 | White, Jr. |
| 4,341,218 A | | 7/1982 | Ü |
| 4,364,392 A | | 12/1982 | Strother et al. |
| 4,383,879 A | | 5/1983 | Le Du et al. |
| 4,441,495 A | | 4/1984 | Hicswa |
| 4,517,979 A | | 5/1985 | Pecenka |
| 4,545,367 A | | 10/1985 | Tucci |
| 4,648,388 A | | 3/1987 | Steffee |
| 4,743,260 A | | 5/1988 | Burton |
| 4,772,287 A | | 9/1988 | Ray et al. |
| 4,887,595 A | | 12/1989 | Heinig et al. |
| 4,892,550 A | * | 1/1990 | Huebsch .................. 623/23.19 |
| 4,904,260 A | | 2/1990 | Ray et al. |
| 4,998,936 A | | 3/1991 | Mehdian |
| 5,000,165 A | | 3/1991 | Watanabe |
| 5,030,220 A | | 7/1991 | Howland |
| 5,037,445 A | | 8/1991 | Sander et al. |
| 5,084,049 A | | 1/1992 | Asher et al. |
| 5,108,404 A | | 4/1992 | Scholten et al. |

(Continued)

FOREIGN PATENT DOCUMENTS

DE    197 26 754 A1    2/1999

(Continued)

OTHER PUBLICATIONS

Bennett, Gregory J., "Lumbosacral Stabilization Using Screw Fixation Techniques," Neurosurgery, McGraw-Hill Health Professions Division, Second Edition, vol II, pp 3027-3035.

(Continued)

*Primary Examiner*—Eduardo C. Robert
*Assistant Examiner*—D. Jacob Davis
(74) *Attorney, Agent, or Firm*—Knobbe, Martens, Olson & Bear, LLP

(57) ABSTRACT

A method of repositioning or fixing a first vertebrae or portion of a first vertebrae comprising fixing a bone screw in the first vertebrae and a bone screw in a second vertebrae, where each bone screw has a portal, and inflating an inflatable balloon between the portals, thereby creating a rigid structure between the bone screws.

8 Claims, 16 Drawing Sheets

U.S. PATENT DOCUMENTS

| | | |
|---|---|---|
| 5,139,499 A | 8/1992 | Small et al. |
| 5,146,933 A | 9/1992 | Boyd |
| 5,165,919 A | 11/1992 | Sasaki et al. |
| 5,171,279 A | 12/1992 | Mathews |
| 5,171,280 A | 12/1992 | Baumgartner |
| 5,176,680 A | 1/1993 | Vignaud et al. |
| 5,181,921 A | 1/1993 | Makita et al. |
| 5,195,970 A * | 3/1993 | Gahara ................ 604/103.08 |
| 5,222,970 A | 6/1993 | Reeves |
| 5,242,443 A | 9/1993 | Kambin |
| 5,242,444 A | 9/1993 | MacMillan |
| 5,324,261 A | 6/1994 | Amundson et al. |
| 5,342,361 A | 8/1994 | Yuan et al. |
| 5,357,983 A | 10/1994 | Mathews |
| 5,397,363 A | 3/1995 | Gelbard |
| 5,470,336 A | 11/1995 | Ling et al. |
| 5,474,551 A | 12/1995 | Finn et al. |
| 5,486,174 A | 1/1996 | Fournet-Fayard et al. |
| 5,496,322 A | 3/1996 | Mathews |
| 5,520,689 A | 5/1996 | Schlapfer et al. |
| 5,529,653 A | 6/1996 | Glastra |
| 5,549,679 A * | 8/1996 | Kuslich ................ 623/17.12 |
| 5,556,429 A | 9/1996 | Felt |
| 5,562,661 A | 10/1996 | Yoshimi et al. |
| 5,562,736 A | 10/1996 | Ray et al. |
| 5,569,248 A | 10/1996 | Mathews |
| 5,571,189 A | 11/1996 | Kuslich |
| 5,584,887 A | 12/1996 | Kambin |
| 5,591,165 A | 1/1997 | Jackson |
| 5,591,167 A | 1/1997 | Laurain et al. |
| 5,591,199 A | 1/1997 | Porter et al. |
| 5,593,408 A | 1/1997 | Gayet et al. |
| 5,649,925 A | 7/1997 | Alacreu |
| 5,658,286 A | 8/1997 | Sava |
| 5,720,751 A | 2/1998 | Jackson |
| 5,728,097 A | 3/1998 | Mathews |
| 5,752,955 A | 5/1998 | Errico |
| 5,772,661 A | 6/1998 | Michelson |
| 5,779,672 A | 7/1998 | Dormandy, Jr. |
| 5,792,044 A | 8/1998 | Foley et al. |
| 5,795,353 A | 8/1998 | Felt |
| 5,800,435 A | 9/1998 | Errico et al. |
| 5,827,289 A | 10/1998 | Reiley et al. |
| 5,888,220 A | 3/1999 | Felt et al. |
| 5,899,939 A | 5/1999 | Boyce et al. |
| 5,910,142 A | 6/1999 | Tatar |
| 5,938,663 A | 8/1999 | Petreto |
| 5,972,015 A | 10/1999 | Scribner et al. |
| 5,980,253 A | 11/1999 | Oxman et al. |
| 6,025,406 A | 2/2000 | Oxman et al. |
| 6,033,406 A | 3/2000 | Mathews |
| 6,042,380 A | 3/2000 | De Rowe |
| 6,043,295 A | 3/2000 | Oxman et al. |
| 6,048,346 A | 4/2000 | Reiley et al. |
| 6,066,154 A | 5/2000 | Reiley et al. |
| 6,080,801 A | 6/2000 | Draenert et al. |
| 6,099,528 A | 8/2000 | Saurat |
| 6,102,912 A | 8/2000 | Cazin et al. |
| 6,106,530 A | 8/2000 | Harada |
| 6,123,707 A | 9/2000 | Wagner |
| 6,126,689 A | 10/2000 | Brett |
| 6,127,597 A * | 10/2000 | Beyar et al. ................ 606/86 |
| 6,149,655 A | 11/2000 | Constantz et al. |
| 6,159,012 A | 12/2000 | Oxman et al. |
| 6,174,334 B1 | 1/2001 | Suddaby |
| 6,175,758 B1 | 1/2001 | Kambin |
| 6,176,882 B1 | 1/2001 | Biedermann et al. |
| 6,206,922 B1 | 3/2001 | Zdeblick et al. |
| 6,226,548 B1 | 5/2001 | Foley et al. |
| 6,235,028 B1 | 5/2001 | Brumfield et al. |
| 6,241,734 B1 | 6/2001 | Scribner et al. |
| 6,280,456 B1 | 8/2001 | Scribner |
| 6,296,644 B1 | 10/2001 | Saurat et al. |
| 6,306,177 B1 | 10/2001 | Felt et al. |
| 6,332,894 B1 | 12/2001 | Stalcup et al. |
| 6,395,034 B1 | 5/2002 | Suddaby |
| 6,402,784 B1 | 6/2002 | Wardlaw |
| 6,425,923 B1 * | 7/2002 | Stalcup et al. ........... 623/23.58 |
| 6,443,988 B1 | 9/2002 | Felt et al. |
| 6,447,514 B1 | 9/2002 | Stalcup |
| 6,530,926 B1 | 3/2003 | Davison |
| 6,530,929 B1 | 3/2003 | Justis et al. |
| 6,558,386 B1 | 5/2003 | Cragg |
| 6,558,390 B1 | 5/2003 | Craig |
| 2001/0004710 A1 | 6/2001 | Felt et al. |
| 2002/0022764 A1 | 2/2002 | Smith et al. |
| 2002/0045904 A1 | 4/2002 | Fuss et al. |
| 2002/0068975 A1 | 6/2002 | Teitelbaum et al. |
| 2002/0082598 A1 | 6/2002 | Teitelbaum |
| 2002/0082600 A1 | 6/2002 | Shaolian et al. |
| 2002/0082601 A1 | 6/2002 | Toyama et al. |
| 2002/0161368 A1 | 10/2002 | Foley et al. |
| 2002/0198526 A1 | 12/2002 | Shaolian et al. |
| 2003/0028251 A1 | 2/2003 | Mathews |
| 2003/0040800 A1 | 2/2003 | Li et al. |
| 2003/0060826 A1 | 3/2003 | Foley et al. |
| 2003/0144624 A1 | 7/2003 | Barbut |
| 2003/0195547 A1 | 10/2003 | Scribner et al. |
| 2004/0006341 A1 | 1/2004 | Shaolian et al. |

FOREIGN PATENT DOCUMENTS

| | | |
|---|---|---|
| RU | 839513 | 5/1981 |
| WO | WO 97/30666 | 8/1997 |
| WO | WO 97/38639 | 10/1997 |
| WO | WO 99/09902 | 3/1999 |
| WO | WO 99/15097 | 4/1999 |
| WO | WO 99/26549 | 6/1999 |
| WO | WO 00/44288 | 8/2000 |

OTHER PUBLICATIONS

Müller, Adolf M.D. et al., "A Keyhole Approach for Endoscopically Assisted Pedicle Screw Fixation in Lumbar Spine Instability," Neurosurgery, 47(1): 85-96 (Jul. 2000).

Kyphon Inc., Kyphon: Fragility Fracture Management: About Kyphon. 2000.

Wilkins, Robert H., M.C. et al., Newrosurgery. 2$^{nd}$ Edition, vol. 1, pp. 3027-3035.

* cited by examiner

PERCUTANEOUS VERTEBRAL FUSION SYSTEM

CROSS-REFERENCE TO RELATED APPLICATION

This Application is a divisional of U.S. patent application Ser. No. 09/747,066, filed Dec. 21, 2000 now U.S. Pat. No. 6,821,277, which takes priority from United States Provisional Patent Application 60/213,385, filed Jun. 23, 2000 entitled "Percutaneous Interbody Fusion Device,", the contents of which are incorporated into this disclosure by reference in its entirety.

BACKGROUND

The human vertebrae and associated connective elements are subject to a variety of diseases and conditions which cause pain and disability. Among these diseases and conditions are spondylosis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

The pain and disability related to these diseases, conditions, injuries and manipulations often results from the displacement of all or part of a vertebra from the remainder of the vertebral column. A variety of methods have been developed to restore the displaced vertebrae or portions of displaced vertebrae to their normal position and to fix them within the vertebral column. For example, open reduction with screw fixation is one currently used method. These methods, however, are associated with a variety of disadvantages, such as high cost, lengthy inpatient hospital stays and the potential morbidity associated with open procedures.

Therefore, there is a need for a method of repositioning and fixing displaced vertebrae or portions of displaced vertebrae to a position within the vertebral column which is more stable or which causes less morbidity. Further, there is a need for a system for performing a method of repositioning and fixing displaced vertebrae or portions of displaced vertebrae to a position within the vertebral column which is more stable or which causes less morbidity.

SUMMARY

According to one embodiment of the present invention, there is provided a bone screw comprising a proximal portion comprising a head with a proximal end and a portal; a distal portion comprising threads and a tip with a distal end; and a central lumen configured to receive a guidewire extending coaxially completely through the bone screw from the proximal end to the distal end. The head comprises a proximal portion configured to mate with the tip of a screwdriver.

According to another embodiment of the present invention, there is provided a screwdriver comprising a proximal end comprising a handle configured to permit grasping of the screwdriver and to permit the application of torque to a bone screw; a distal end comprising a shaft having a tip configured to interface with a bone screw; and a central lumen configured to receive a guidewire extending coaxially completely through the screwdriver from the proximal end to the distal end.

According to yet another embodiment of the present invention, there is provided an inflatable connection rod comprising a proximal end comprising a self-sealing valve; a distal end comprising a tip; and a compliant, inflatable balloon between the proximal end and the distal end. The balloon comprises thin, reinforcing wires.

According to another embodiment of the present invention, there is provided a directing sheath comprising a proximal portion with a proximal end; a distal portion with a distal end; a central portion between the proximal portion and the distal portion comprising at least two openings; and a lumen extending through the directing sheath from the proximal end to distal end. The directing sheath is preferably scored along its longitudinal axis to allow the directing sheath to be split into two separate halves by peeling the directing sheath apart at either its proximal end or its distal end or both along the scoring.

In a preferred embodiment of the present invention, there is provided a method of repositioning or fixing one or more unstable, separated or displaced vertebrae or one or more portions of one or more vertebrae in a patient's vertebral column. The method comprises:

a) identifying a patient who is a suitable candidate for undergoing the method;

b) making a stab incision in the patient's skin overlying the patient's vertebral column at or near the level of the vertebrae or portion of vertebrae to be repositioned or fixed;

c) creating a first tract from the incision to the posterior periosteal surface of the vertebrae;

d) incising the periosteum and extending the first tract into the cortex of the vertebrae;

e) inserting a first guidewire into the first tract;

f) advancing a bone screw comprising a portal and a tip, and a screwdriver over the first guidewire;

g) applying torque to the bone screw using the screwdriver, thereby fixing part of the tip of the bone screw into the vertebrae while the portal of the bone screw is exterior and dorsal to the vertebrae and the portal is open parallel to the long axis of the vertebral column;

h) removing the screwdriver and the first guidewire;

i) repeating c) through h) for at least one vertebrae which is neither unstable, separated or displaced and which is adjacent the vertebrae or portion of the vertebrae that is being repositioned or fixed, or repeating c) through h) for the cranial-ward portion of the sacrum of the patient;

j) inserting an inflatable connection rod comprising a proximal end, a distal end and an inflatable balloon between the proximal end and the distal end, between the portals of the bone screws; and k) inflating the inflatable balloon thereby creating a rigid structure between the inflated inflatable connection rod and the bone screws;

thereby repositioning or fixing the one or more unstable, separated or displaced vertebrae or the one or more portions of one or more vertebrae unilaterally.

Identifying a patient who is a suitable candidate comprises identifying a patient who has one or more unstable vertebrae, one or more portions of a vertebrae at least partly separated from the remainder of the vertebrae with potential or complete separation, or who has one or more vertebrae or a portion of one or more vertebrae displaced from its normal position relative to the vertebral column, or who has one or more portions of a vertebrae at least partly separated from the remainder of the vertebrae and displaced from its normal position relative to the vertebral column; and where the patient has either pain, loss of function or real or potential instability which is likely due to the separation or displacement, or separation and displacement.

The method can comprise enlarging the first tract from the incision to the posterior periosteal surface using a high-pressure fascial dilator balloon after creating the first tract. Further, inserting an inflatable connection rod can comprise:

i) percutaneously inserting a hollow needle and advancing the hollow needle to the portal of one of the bone screws;

ii) introducing a second guidewire through the lumen of the hollow needle and into the portal of one of the bone screws; and iii) passing the second guidewire through all of the portals in the bone screws, thereby creating a second tract.

The method can also comprise:

i) dilating the second tract created by the second guidewire using a high pressure balloon;

ii) passing an introducer sheath over the guidewire along the entire guidewire second tract;

iii) removing the guidewire; and iv) advancing the inflatable connection rod through the introducer sheath until the inflatable connection rod advances between the bone screw portals.

The method can also comprise using a guidewire directing device to direct the advancing second guidewire through at least one bone screw portal, or can comprise using a guidewire capture device to pull the second guidewire through the patient's skin. Further, inflating the inflatable balloon can comprise inflating the balloon with a rapid setting, liquid polymer.

In a particularly preferred embodiment, the method further comprises repeating c) through h) for one additional vertebrae, where the one additional vertebrae is either unstable, separated or displaced, or where one or more portions of the one additional vertebrae is unstable, separated or displaced. In another particularly preferred embodiment, the method further comprises repeating b) through k) on the opposite side of the spinous processes of the patient's vertebrae column, thereby repositioning or fixing the one or more unstable, separated or displaced vertebrae or the one or more portions of one or more vertebrae bilaterally.

In a preferred embodiment, the method further comprises using a directing sheath to position the bone screws.

According to another embodiment of the present invention, there is provided a method of repositioning or fixing a first vertebrae that is unstable, separated or displaced or that has one or more unstable, separated or displaced portions. The method comprises:

a) fixing one or more than one bone screw in the first vertebrae and one or more than one bone screw in a second vertebrae;

b) inserting an inflatable balloon between the portal of the bone screw in the first vertebrae and the portal of the bone screw in the second vertebrae; and c) inflating the inflatable balloon thereby creating a rigid structure between the balloon and the bone screws;

thereby repositioning or fixing the first vertebrae or portion of the first vertebrae.

In a preferred embodiment, the method further comprises advancing each bone screw over a guidewire before a). In another preferred embodiment, a) comprises applying torque to each bone screw using a screwdriver advanced over a guidewire. In another preferred embodiment, c) comprises inflating the balloon with a rapid setting, liquid polymer.

In a particularly preferred embodiment, the method further comprises repeating a) through c) on the opposite side of the spinous processes of the patient's vertebrae column, thereby bilaterally repositioning or fixing the one or more unstable, separated or displaced vertebrae or the one or more portions of one or more vertebrae. In a preferred embodiment, the method further comprises using a directing sheath to position the bone screws before a).

According to another embodiment of the present invention, there is provided a kit for repositioning or fixing a first vertebrae that is unstable, separated or displaced or that has one or more unstable, separated or displaced portions. The kit comprises one or more devices selected from the group consisting of a bone screw according to the present invention, a screwdriver according to the present invention, an inflatable connection rod according to the present invention, and a directing sheath according to the present invention.

FIGURES

These and other features, aspects and advantages of the present invention will become better understood from the following description, appended claims, and accompanying figures where:

DESCRIPTION

In one embodiment of the present invention, there is provided a method of repositioning or fixing one or more unstable, separated or displaced vertebrae or one or more portions of one or more vertebrae such that the one or more unstable, separated or displaced vertebrae or portions are more stable or are associated with less morbidity. In another preferred embodiment, there is provided a system for performing a method of repositioning or fixing one or more unstable, separated or displaced vertebrae or one or more portions of one or more vertebrae such that the one or more unstable, separated or displaced vertebrae or portions are associated with less morbidity.

The method of the present invention can be used to reposition or fix one or more unstable, separated or displaced vertebrae or one or more portions of one or more vertebrae in the cervical, thoracic or lumbar regions of the vertebral column. Additionally, the method can be used to reposition or fix one or more unstable, separated or displaced vertebrae or one or more portions of one or more vertebrae in the lumbar region, using the cranial-ward portion of the sacrum and the "vertebrae" against which the lumbar vertebrae or portion is anchored.

As used in this disclosure, "morbidity" comprises pain, loss of function, instability and increased tendency to degenerate, as well as other aspects of morbidity, as will be understood by those with skill in the art with reference to this disclosure.

As used in this disclosure, the term "fixed" with respect to a vertebra comprises stabilizing the vertebra.

As used in this disclosure, the phrase "repositioned or fixed" and its grammatical permutations means repositioned, or fixed or both repositioned and fixed.

Figure 1:
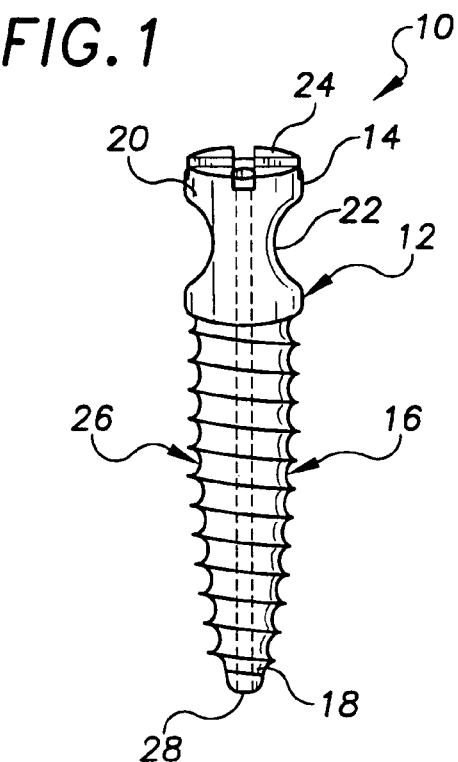
FIG. 1 shows an elevated perspective view of a bone screw according to the present invention along the proximal to distal axis.
Figure 2:
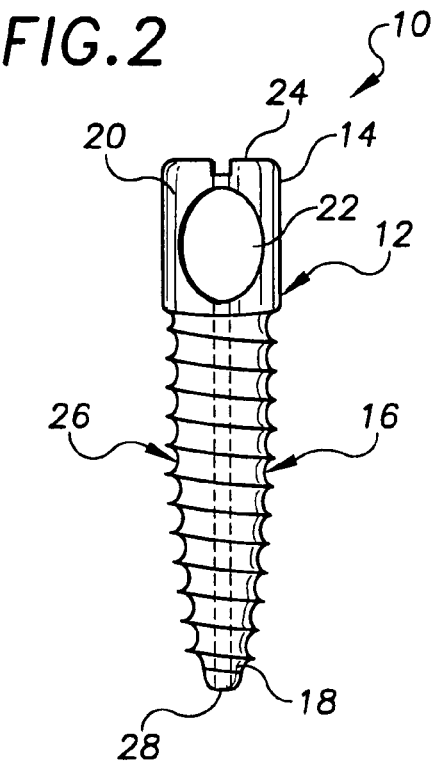
FIG. 2 shows the bone screw of FIG. 1 rotated ninety degrees around its proximal to distal axis.
Figure 3:
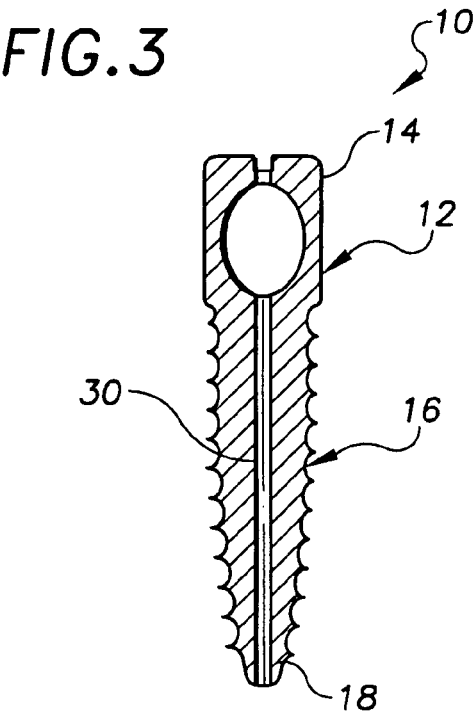
FIG. 3 shows a cutaway, elevated perspective view of the bone screw shown in FIG. 2 along the proximal to distal axis.

The system of the present invention comprises several devices, some of which will now be disclosed in detail. Referring now to FIG. 1 and FIG. 2, there are shown two elevated perspective views of a bone screw according to the present invention along the proximal to distal axis, where FIG. 2 shows the bone screw in FIG. 1 rotated ninety degrees around its proximal to distal axis. Referring now to FIG. 3, there is shown a cutaway, elevated perspective view of the bone screw shown in FIG. 2 along the proximal to distal axis. In one embodiment, the bone screw is made of a biocompatible material such as titanium or stainless steel. In one embodiment, the bone screw has a proximal length to distal length of between about 40 mm and about 60 mm. In a particularly preferred embodiment, the bone screw has a proximal length to distal length of about 50 mm.

Figure 4:
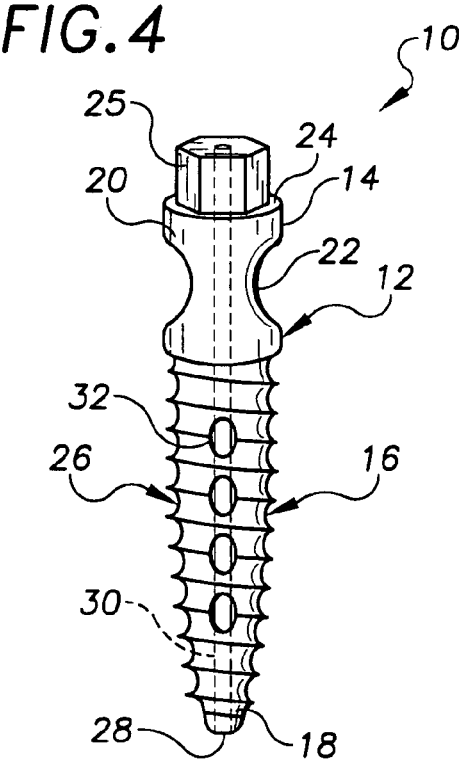
FIG. 4 shows another embodiment of the bone screw according to the present invention along the proximal to distal axis.

As can be seen, the bone screw 10 comprises a proximal portion 12 with a proximal end 14 and a distal portion 16 with a distal end 18. The proximal portion 12 comprises a head 20 and a portal 22. In a preferred embodiment, the head 20 comprises a proximal portion 24 configured to mate with the tip of a screwdriver (not shown). In a particularly preferred embodiment, the top 24 portion comprises a slot. In another particularly preferred embodiment, as shown, the proximal portion 24 is configured to mate with a Phillips head screwdriver. Other indentation configurations are also suitable, as will be understood by those with skill in the art with reference to this disclosure. For example, as shown in FIG. 4, the proximal portion 24 can comprise a raised platform 25 having a plurality of substantially straight sides, such as a hexagonal platform, configured to mate with a corresponding depression in the distal end of a screwdriver.

The portal 22 of the bone screw extends through the head 20 and is preferably between about 4 mm and about 8 mm in minimum diameter in the proximal to distal plane and is preferably either oval or round in shape when viewed perpendicular to the proximal to distal plane. In a particularly preferred embodiment, the portal 22 is about 6 mm in minimum diameter in the proximal to distal plane.

The distal portion 16 of the bone screw 10 comprises threads 26 and a sharp tip 28. Additionally, the bone screw 10 comprises a central lumen 30 extending coaxially completely through the bone screw 10 from the proximal end 14 to the distal end 18 and configured to receive a guidewire used in the present method. Preferably, but not essentially, the bone screw comprises one or more than one perforation 32. The one or more than one perforation can extend into the central lumen 30, or can extend completely laterally through the distal portion 16. Additionally, the one or more than one perforation 32 can be aligned axially, as shown, or can be staggered axially, not shown. The one or more than one perforation 32 permits bone to grow into the bone screw 10 and help stabilize the bone screw 10 within the bone. Additionally, bone matrix material such as a hydroxyapatite preparation can be injected into the central lumen 30 and through the one or more than one perforation 32 to promote bone ingrowth.

Figure 5:
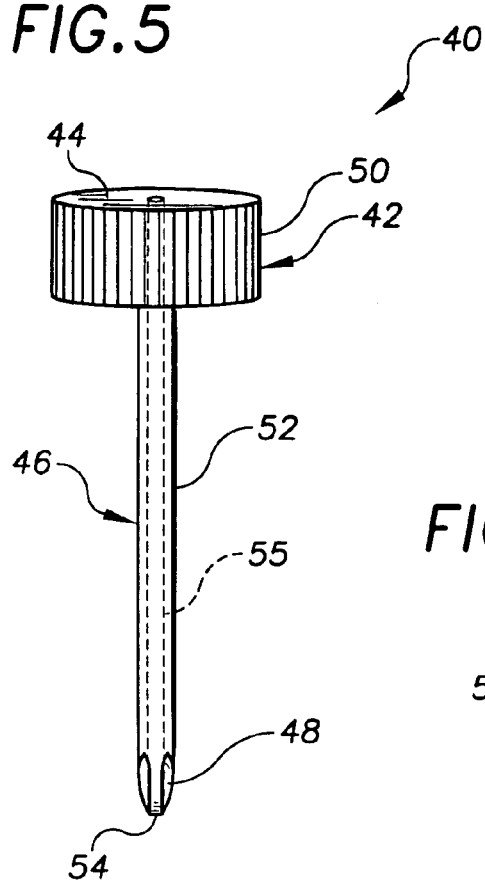
FIG. 5 and FIG. 6 shows elevated perspective views of two screwdrivers according to the present invention along the proximal to distal axis.
Figure 6:
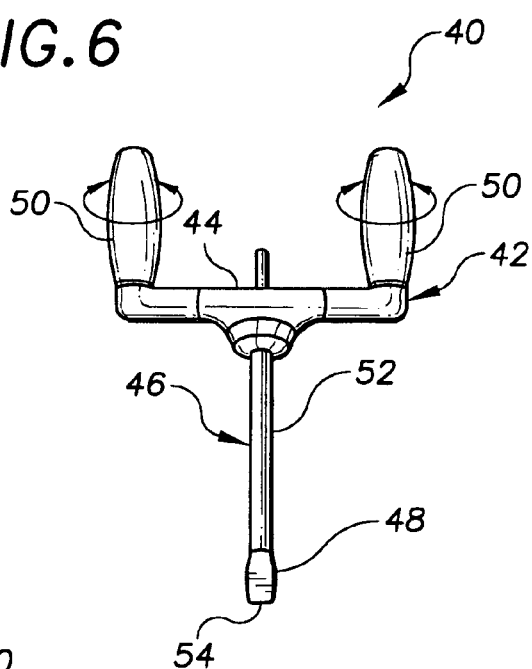

The system of the present invention further comprises a screwdriver configured to apply torque to the bone screw. Referring now to FIG. 5 and to FIG. 6, there are shown elevated perspective views of two embodiments of a screwdriver 40 according to the present invention along the proximal to distal axis. As can be seen, the screwdriver comprises a proximal portion 42 comprising a proximal end 44 and a distal portion 46 comprising a distal end 48. The proximal portion 42 comprises handles 50 configured to permit grasping of the screwdriver and to permit the application of torque to a bone screw. Various configurations of the proximal end are possible, as will be understood by those with skill in the art with reference to this disclosure. Preferably, the handles 50 should be able to rotate around their axis independently of each other.

The distal portion 46 of the screwdriver 40 comprises a shaft 52 having a tip 54 configured to interface with the proximal portion of a bone screw according to the present invention. Therefore, the configuration of the distal end 48 will depend upon the configuration of the head of the bone screws being used in conjunction with the screwdriver 40. The screwdriver 40 further comprises a central lumen 55 extending coaxially completely through the screwdriver 40 from the proximal end 44 to the distal end 48 and configured to receive a guidewire used in the present method.

Figure 7:
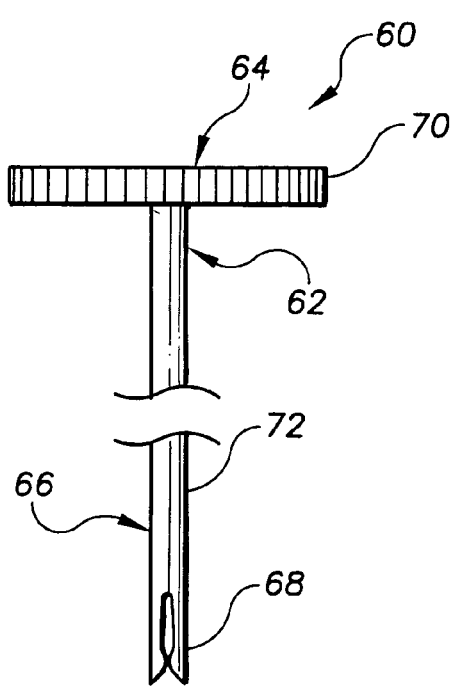
FIG. 7 shows an elevated perspective view of a guidewire directing device according to the present invention along the proximal to distal axis.

The system of the present invention can optionally comprise a guidewire directing device. Referring now to FIG. 7, there is shown an elevated perspective view of a guidewire directing device 60 according to the present invention along the proximal to distal axis. As can be seen, the guidewire directing device 60 comprises a proximal portion 62 with a proximal end 64 and a distal portion 66 with a distal end 68. The proximal portion 62 comprises a handle 70. Preferably, the handle 70 is configured to assist in grasping and manipulating the handle 70. The distal portion 66 comprises a shaft 72 having a fork-tipped end 68. The guidewire directing device 60 is used to percutaneously alter the direction of an advancing guidewire by engaging the guidewire in the fork-tipped end 68, rotating the handle 70 and advancing and withdrawing the handle 70 along the proximal to distal axis, thereby altering the direction of the advancing guidewire.

Figure 8:
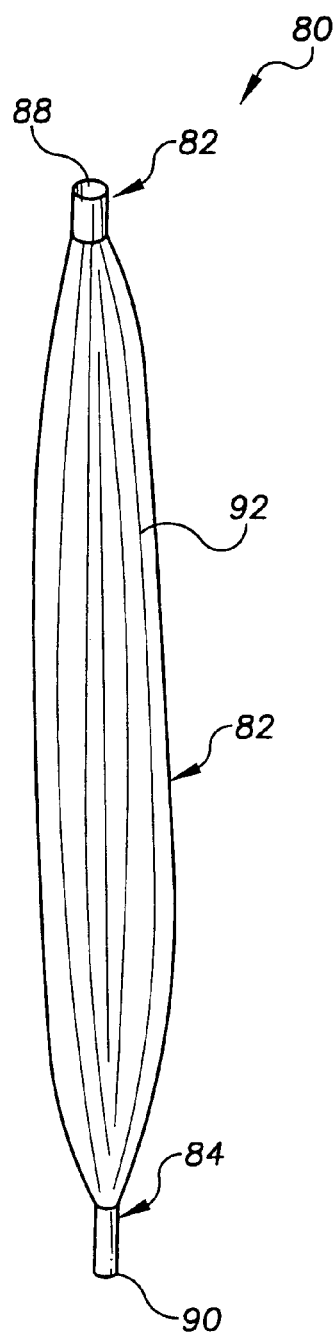
FIG. 8 shows an elevated perspective view of an inflatable connection rod elevated according to the present invention along the proximal to distal axis.

The system of the present invention further comprises an inflatable connection rod. Referring now to FIG. 8, there is shown an elevated perspective view of an inflatable connection rod according to the present invention along the proximal to distal axis in the uninflated state. The rod 80 comprises a proximal end 82, a distal end 84 and a compliant, inflatable balloon 86 between the proximal end 82 and the distal end 84. The proximal end 82 comprises a self-sealing valve 88. The distal end 84 comprises a tip 90, preferably comprising a biocompatible metal. The balloon comprises any suitable material, but preferably comprises a biocompatible-braided polymer, such as for example a material selected from the group consisting of nylon, polyethylene and polyurethane. Further preferably, the balloon 86 comprises thin, reinforcing metallic wires 92 running the entire proximal to distal length of the lumen of the balloon 86, but separate from the balloon wall. The wires 92 increase the tensile strength of the balloon 86 when inflated, as will be understood by those with skill in the art with reference to this disclosure. The wires 92 preferably comprise titanium or nitinol, but can comprise another suitable material as will be understood by those with skill in the art with reference to this disclosure.

Figure 9:
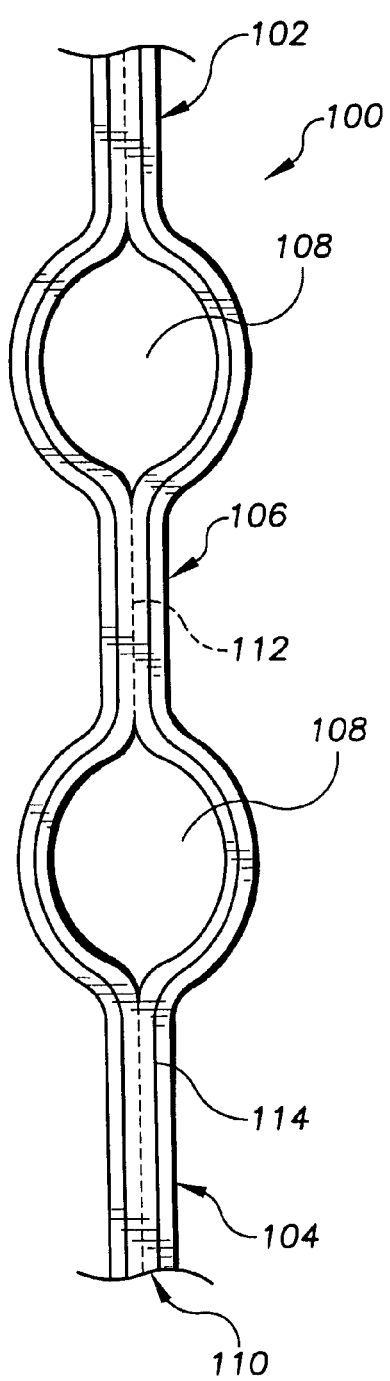
FIG. 9 shows a top perspective view of a directing sheath according to the present invention along the proximal to distal axis.

The system of the present invention can optionally comprise a directing sheath that assists in aligning a structure such as a guidewire or inflatable connection rod to pass through the portals in the bone screws according to the present invention. Referring now to FIG. 9, there is shown a top perspective view of a directing sheath according to the present invention along the proximal to distal axis. As can be seen, the directing sheath 100 comprises a proximal portion 102 with a proximal end (not shown), a distal portion 104 with a distal end (not shown), and a central portion 106 between the proximal portion 102 and the distal portion 106. The central portion 106 comprises at least two openings 108 sized substantially the same as the portal on a bone screw according to the present invention, or slightly larger. The directing sheath 100 has a lumen 110 extending through its entire length from the proximal end to the distal end. The lumen 110 is of sufficient internal diameter to allow a structure such as a guidewire or inflatable connection rod to pass through the directing sheath between the proximal end and distal end. The directing sheath 100 is scored 112 along its longitudinal axis, on either one line or preferably on two opposing lines, to allow the directing sheath 100 to be split into two separate halves by peeling the directing sheath 100 apart at either its proximal end or its distal end or both along the scoring 112. The scoring 112 can be partially or completely through the sheath wall as will be understood by those with skill in the art with reference to this disclosure.

The directing sheath 100 preferably comprises a biocompatible polymer, though other materials are suitable, as will be understood by those with skill in the art with reference to this disclosure. The directing sheath 100 further preferably comprises a radiopaque filament 114 passing around each opening in the central portion, and more preferably running the entire longitudinal length of the directing sheath from the proximal end to the distal end. This filament 114 aids in localizing the directing sheath 100 once it has been percutaneously placed.

The method of the present invention involves percutaneously inserting one or more fusion devices into two or more than two adjacent vertebrae, either unilaterally or, preferably bilaterally, where a portion or all of at least one of the vertebrae is unstable, separated or displaced. The fusion devices reposition or fix the displaced vertebra or portion of the displaced vertebra to a position within the vertebral column which is more stable or which causes less morbidity.

Referring now to FIG. 10 through FIG. 19, there are shown a series of drawings depicting various stages of the method of repositioning and fixing a displaced vertebra or portion of a displaced vertebra, unilaterally, according to the present invention. FIGS. 9–18 show partial cutaway, perspective, midline sagittal views of a portion of a vertebral column undergoing the method of the present invention.

The method will now be disclosed and depicted with reference to only two vertebrae, one which is either unstable, separated or displaced and one of which is neither unstable, separated nor displaced. However, the method can also be applied to three or more vertebrae simultaneously, as will be understood by those with skill in the art with reference to this disclosure. Additionally, the method can be used to stabilize the L5 vertebrae, using the cranial-ward portion of the sacrum as the "vertebrae" with which L5 is anchored. Further, though the method is disclosed and depicted as applied on the left side of the vertebral column, the method can also be applied on the right side of the vertebral column or, preferably, can be applied on both sides of the vertebral column simultaneously, as will be understood by those with skill in the art with reference to this disclosure.

First, the present method comprises identifying a patient who is a suitable candidate for undergoing the method. A suitable candidate has one or more unstable vertebrae, one or more portions of one or more vertebrae at least partly separated from the remainder of the vertebrae with potential or complete separation, or has one or more vertebrae or a portion of one or more vertebrae displaced from its normal position relative to the vertebral column, or has one or more portions of one or more vertebrae at least partly separated from the remainder of the vertebrae and displaced from its normal position relative to the vertebral column. Further, the suitable candidate will preferably have either pain, loss of function or real or potential instability which is likely due to the separation or displacement, or separation and displacement. If only a portion of the vertebra is unstable, separated or displaced, the portion of the vertebra that is unstable, separated or displaced will generally include at least part of the vertebral body and adjoining pedicle. However, other unstable, separated or displaced portions of a vertebra can be repositioned or fixed using the present method, as will be understood by those with skill in the art with reference to this disclosure. For example, a suitable patient can have a disease or condition such as spondylosis, spondylolisthesis, vertebral instability, spinal stenosis and degenerated, herniated, or degenerated and herniated intervertebral discs, though actual indications require the expertise of one of skill in the art as will be understood by those with skill in the art with reference to this disclosure.

Next, the present method comprises making a stab incision in the patient's skin overlying the patient's vertebral column at or near the level of the vertebrae or portion of vertebrae to be repositioned or fixed. In a preferred embodiment, the incision is made at or near the level of the pedicle of the vertebrae or portion of vertebrae to be repositioned or fixed. The pedicle level is located preferably by identifying the pedicle shadow using fluoroscopy. In a preferred embodiment, the stab incision is made using a #11 scalpel blade.

Figure 10:
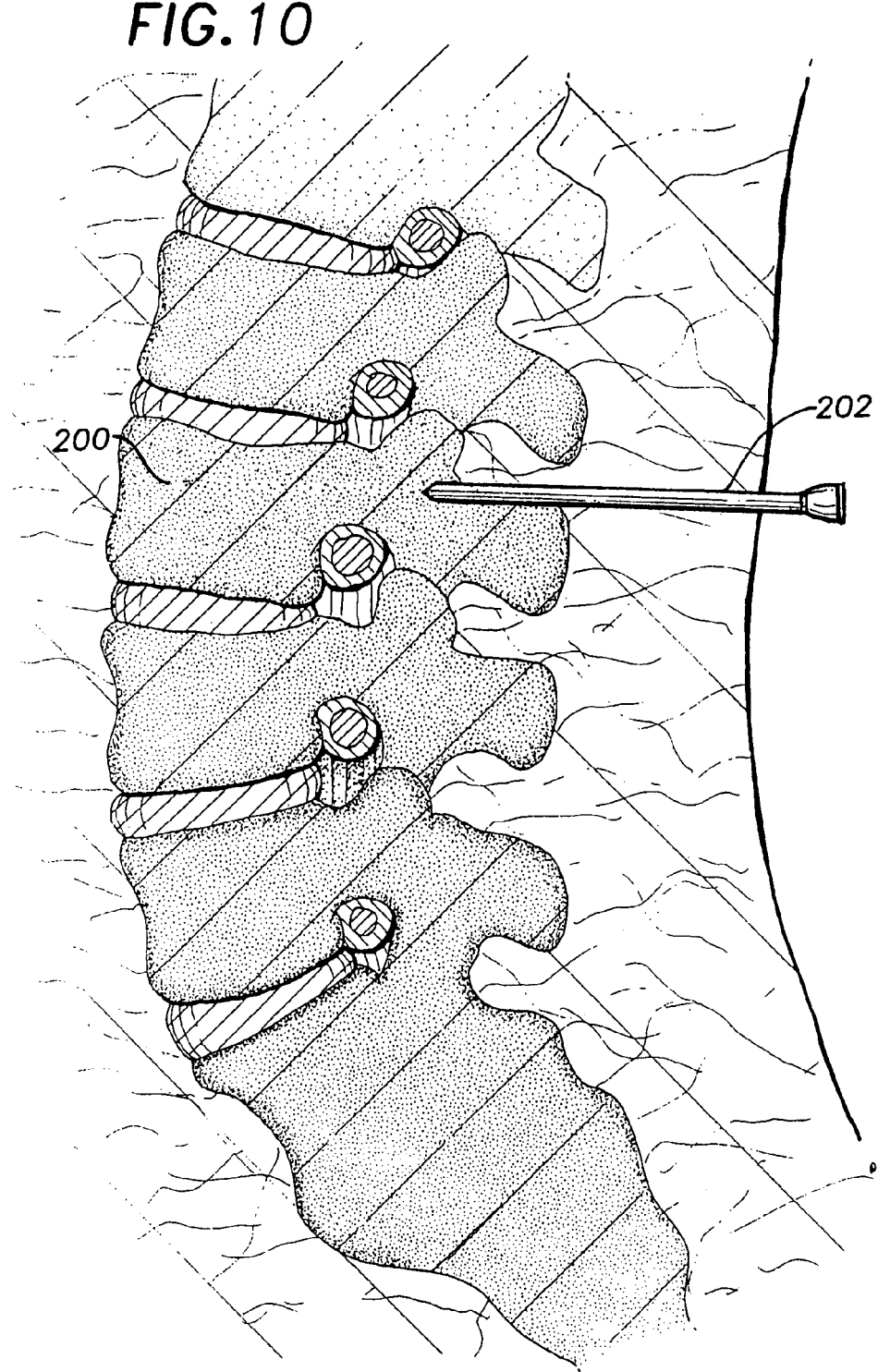
FIG. 10 through FIG. 20 show partial cutaway, perspective, midline sagittal views of a portion of a vertebral column undergoing the method of the present invention.

Then, as shown in FIG. 10, an 11-gauge bone biopsy needle or its equivalent is placed through the stab incision to create a tract to the posterior periosteal surface of the vertebrae 200 which is to be stabilized, repositioned or fixed. Next, the biopsy needle 202 is used to make a small incision in the periosteum and into the cortex of the vertebrae.

Figure 11:
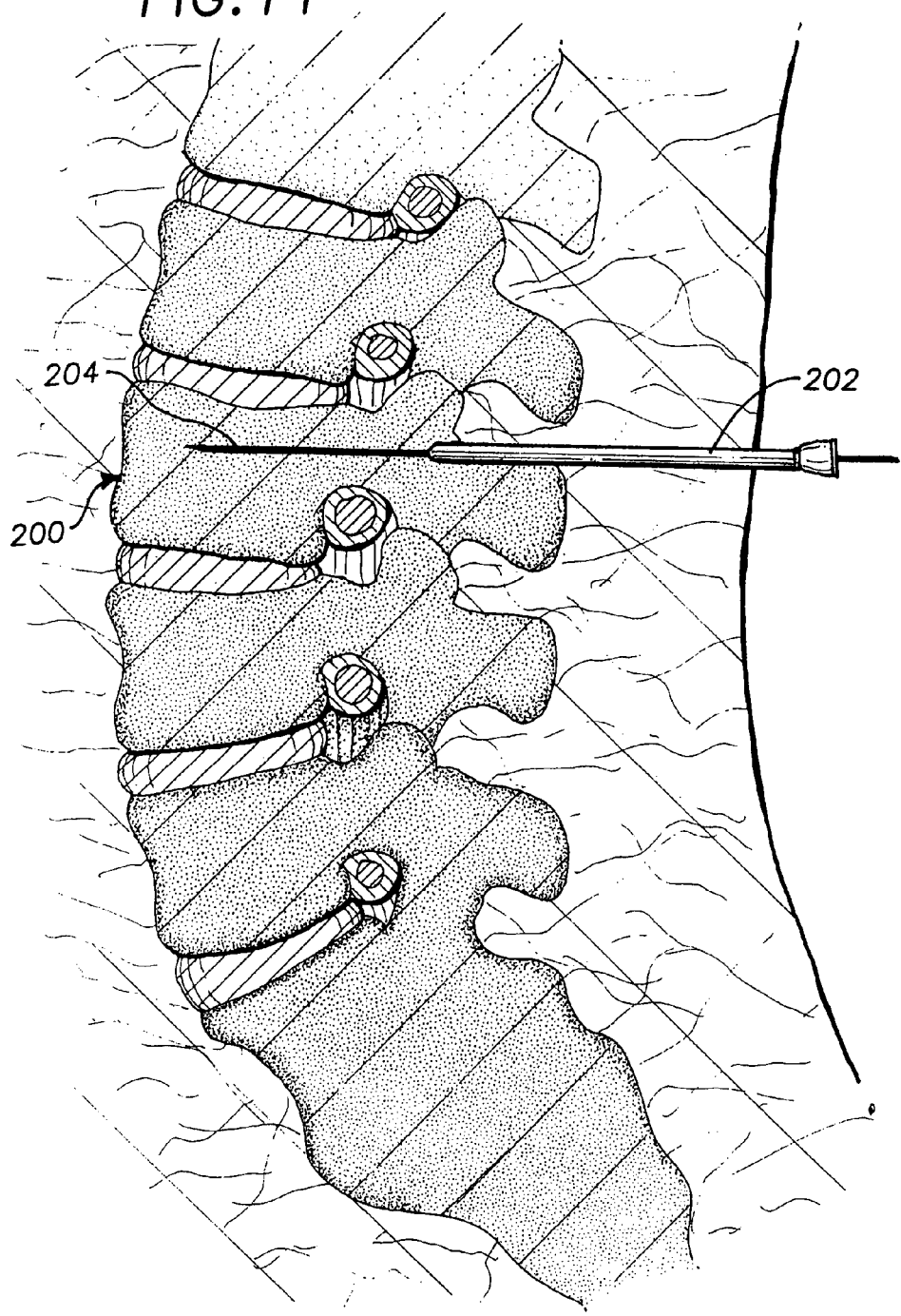

Then, as shown in FIG. 11, a rigid, needle-tipped guidewire 204 having a needle diameter of 13 or 15-gauge is inserted through the biopsy needle 202 into the tract, through the periosteal incision and into the cortex of the bone, and the guidewire 204 is advanced into the anterior aspect of the vertebral body 200 or into another suitable portion of the vertebrae 200, as will be understood by those with skill in the art with reference to this disclosure. Insertion of the guidewire 204 is preferably accomplished using fluoroscopy. This process creates a continuous tract from the skin surface into the anterior vertebral body or suitable portion of the vertebrae 200.

The biopsy needle 202 is then removed and the tract from the skin surface to the nicked periosteal surface is enlarged by using a high-pressure fascial dilator balloon (not shown) over the needle-tipped guidewire. Then, the balloon is removed and a working sheath 206 is introduced into the dilated tract. Alternately, a metallic sheath with a central dilator is advanced over the guidewire from the skin surface to the periosteal surface.

Figure 12:
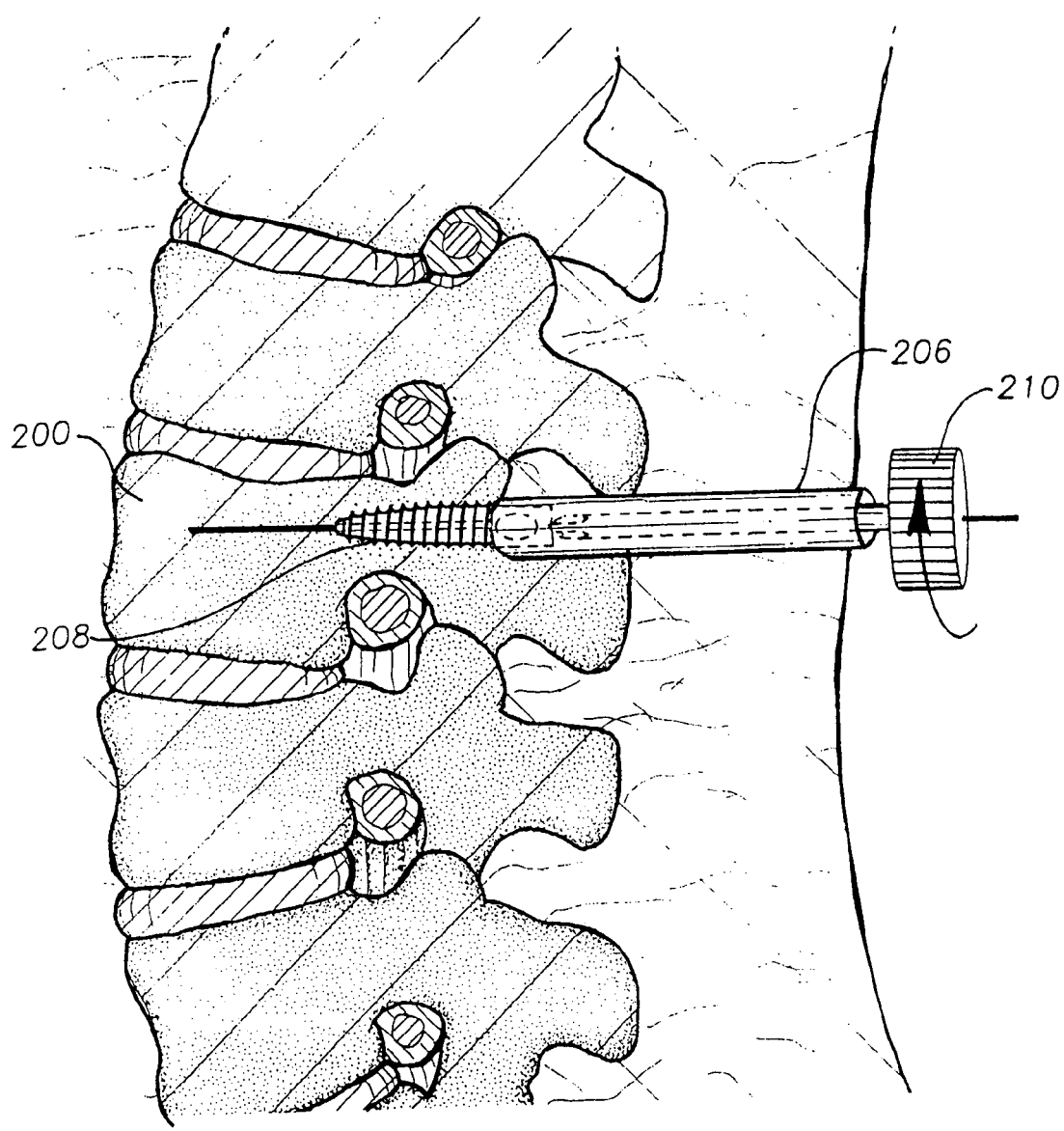
Figure 13:
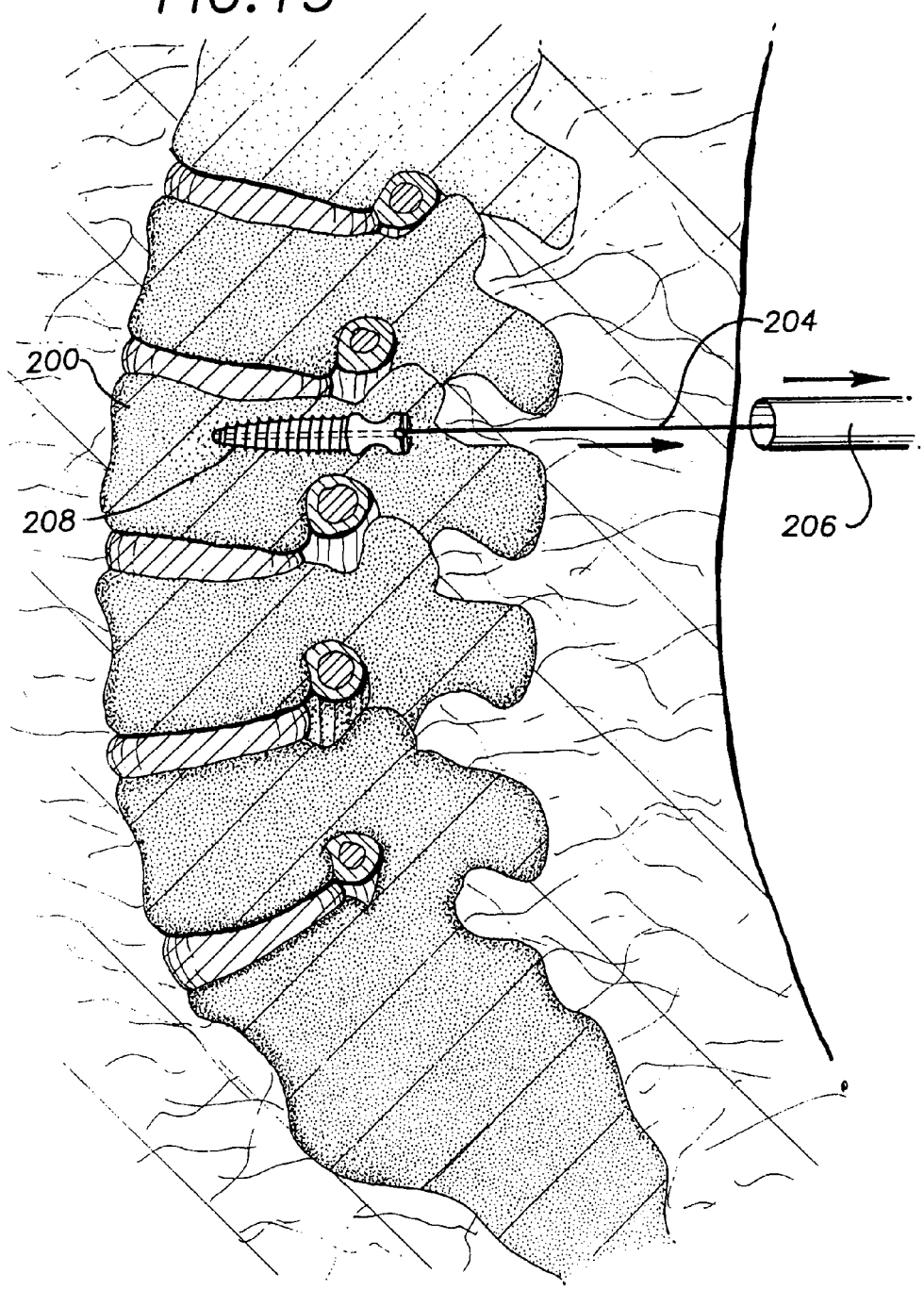

Next, as shown in FIG. 12, a bone screw 208 according to the present invention is introduced into the working sheath 206 over the guidewire 204 by introducing the central lumen of the bone screw 208 over the proximal end of the guidewire 204. A screwdriver 210 according to the present invention is similarly introduced over the guidewire 204. The bone screw 208 and distal portion of the screwdriver 210 are then advanced distally through the sheath 206 and the tract to the periosteal surface of the vertebral 200 until the proximal portion of the bone screw 208 is engaged by the tip of the screwdriver 210. Torque is applied to the bone screw 208 using the screwdriver 210 and the bone screw 208 is advanced until the distal portion of the bone screw 208 enters the anterior vertebral body or other suitable portion of the vertebra 200, while the portal of the bone screw 208 is exterior and dorsal to the vertebra 200 and the portal is open parallel to the long axis of the vertebral column. Then, as shown in FIG. 13, the guidewire 204, sheath 206 and screwdriver 210 are removed after satisfactory placement of the bone screw 208 has been obtained and confirmed by fluoroscopy. Additionally, bone matrix material such as a hydroxyapatite preparation can be injected into the central lumen of the bone screw and through the one or more than one perforation, if present, to promote bone ingrowth.

The stages disclosed above are repeated for at least one additional vertebra 212 until each vertebra that is to be repositioned or fixed has a bone screw 208 applied, and additionally for at least one vertebra which is neither unstable, separated nor displaced and which lies adjacent the cranial-most or caudal-most vertebra that is being repositioned or fixed. The bone screw 208 placed into the vertebra 212 which is neither unstable, separated nor displaced is used as the anchor to reposition or fix each vertebra 200 which is unstable, separated or displaced as follows. As will be understood by those with skill in the art with reference to this disclosure, the bone screws can be placed into the vertebrae in a different order to that described above.

After a bone screw is positioned in each vertebra, the portals are connected using an inflatable connection rod according to the present invention where the rod is inserted between the portals of the bone screws and inflated to create a rigid structure with the bone screws, thereby repositioning and fixing the one or more than one previously unstable, separated or displaced vertebra, or one or more previously unstable, separated or displaced portions of one or more vertebrae with the vertebra that is neither unstable, separated nor displaced. Connection of the bone screws with the inflatable rod is accomplished as follows.

Figure 14:
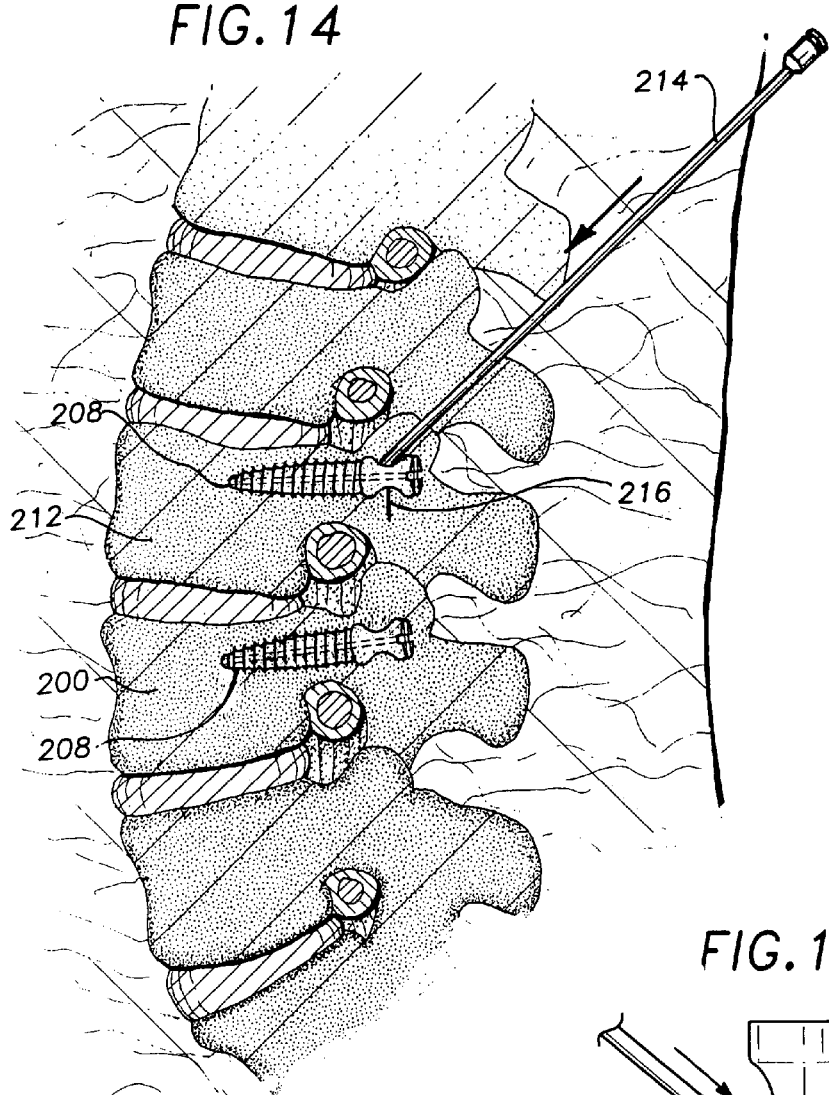
Figure 15:
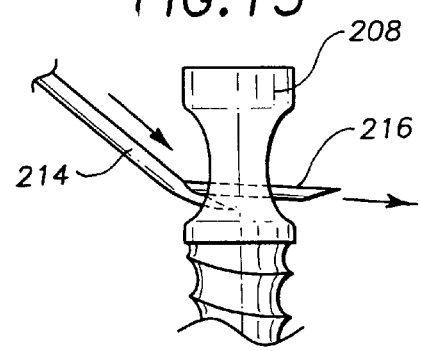

Referring now to FIG. 14 and FIG. 15, a hollow needle 214, such as a 16 gauge or 18 gauge needle, is inserted percutaneously and fluoroscopically advanced to the portal of one of the bone screws 208. While the hollow needle is shown engaging the bone screw 208 in the cranial-ward vertebrae 212, the hollow needle can engage the bone screw 208 in the caudal-ward vertebrae 200 first, as will be understood by those with skill in the art with reference to this disclosure. FIG. 15 is a detailed view of FIG. 14.

Figure 16:
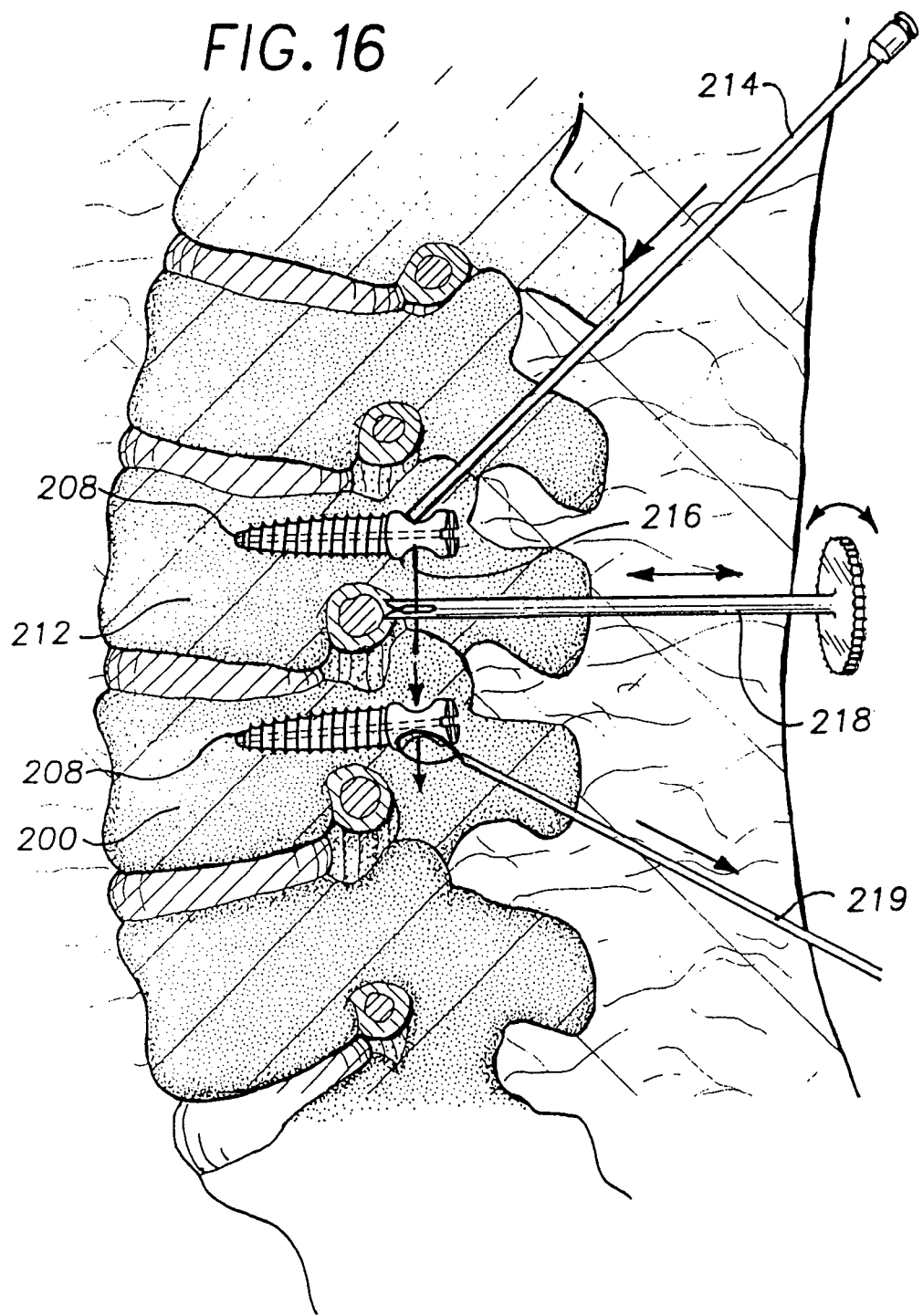

Then, as shown in FIG. 16, a needle-tipped, semi-rigid guidewire 216 is introduced through the lumen of the hollow needle 214 and into the portal of the bone screw 208 in the cranial-ward vertebrae 212. The hollow needle 214 preferably has a Tuohy needle tip which causes the guidewire 216 to exit the hollow needle 214 perpendicular to the distal-proximal axis of the bone screw 208, thereby orienting the guidewire 216 perpendicular to the aligned portals in each bone screw 208 and parallel to the long axis of the vertebral column. Alternately, the hollow needle 214 can have an angled-tip modified Ross needle or other suitable structure as will be understood by those with skill in the art with reference to this disclosure.

In a preferred embodiment, as further shown in FIG. 16, a guidewire 218 directing device according to the present invention is inserted percutaneously between the portals of each bone screw 208 and the fork-tipped end is used to direct the advancing guidewire 216 through the second bone screw portal, and to reorient the guidewire 216 after the guidewire 216 has passed through the portal on the bone screw 208 of the caudal-ward vertebrae 212.

In another preferred embodiment, as further shown in FIG. 16, a guidewire capture device 219, such as a snare or grasping forceps, is inserted percutaneously, caudal to the portal of the bone screw in the caudal-ward vertebrae. The capture device 219 engages the guidewire after it passes through the portal of the bone screw in the caudal-ward vertebrae and allows the distal end of the guidewire to be pulled through the skin posteriorly to obtain control of both the proximal and distal ends of the guidewire.

In another preferred embodiment, the needle-tipped, semi-rigid guidewire 216 comprises an outer helical, flat wire sheath and an inner retractable sharp tip stylet. Once the needle-tipped, semi-rigid guidewire is placed, the stylet can be removed to allow for easier capture by the capture device with less trauma to the surrounding tissue.

Figure 17:
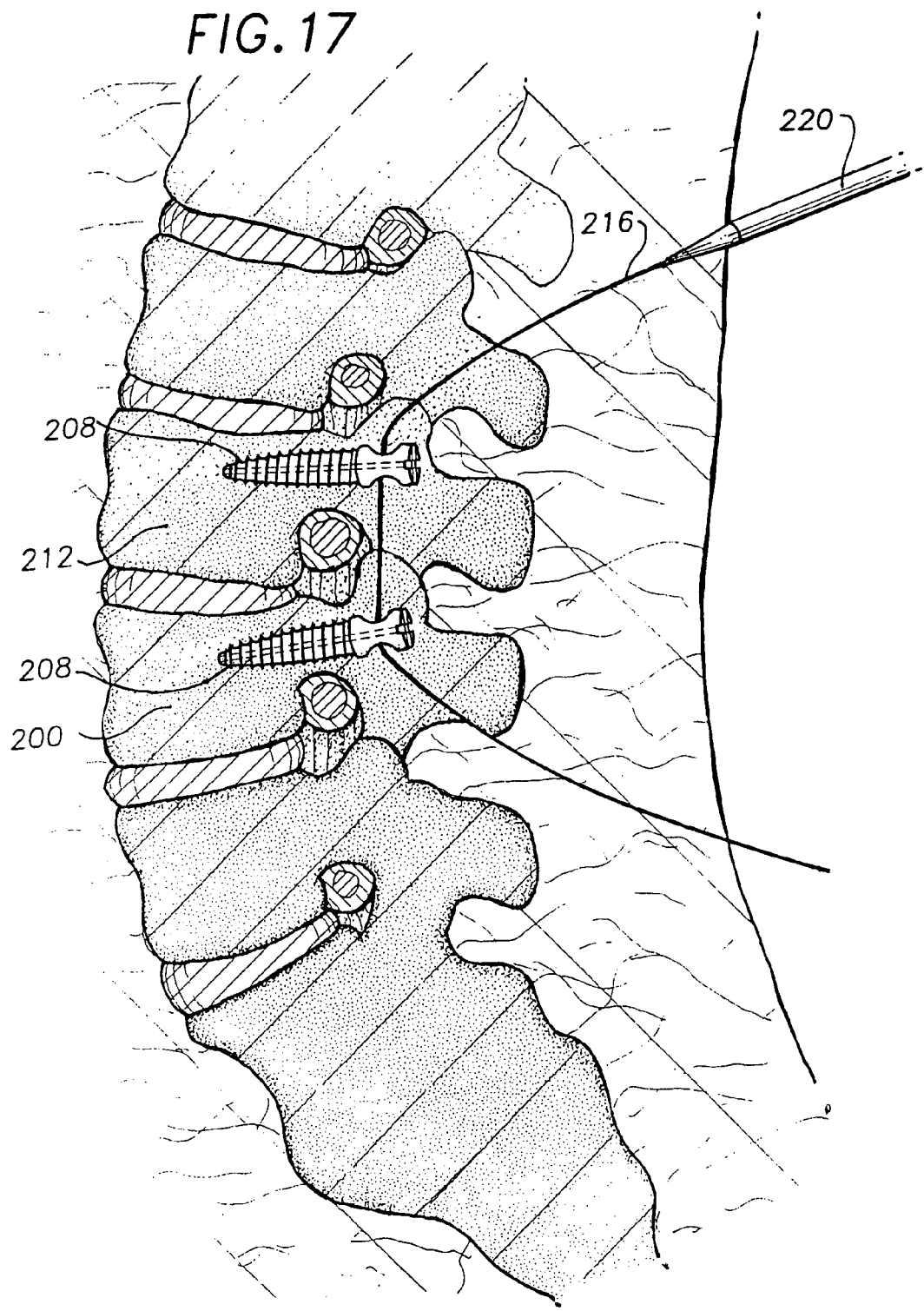

Then, as shown in FIG. 17, the entire guidewire tract is dilated using a high pressure balloon and a flexible introducer sheath 220 is passed over the guidewire 216 along the entire guidewire tract exiting the caudal-ward stab incision. The guidewire 216 is removed after the introducer sheath 220 is placed.

Figure 18:
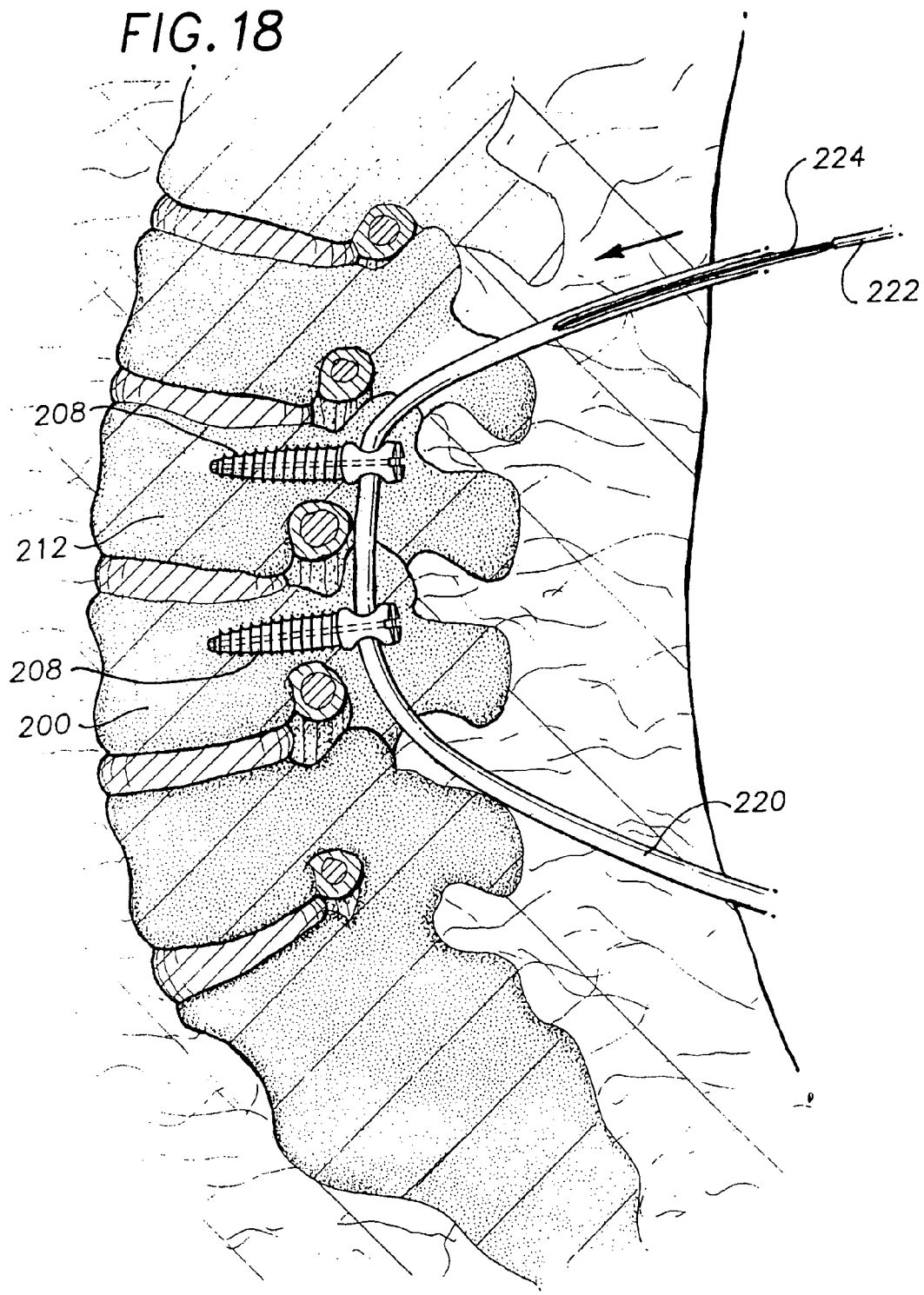

Next, as shown in FIG. 18, an uninflated, inflatable connection rod 222 according to the present invention which is attached to a proximal pushing catheter 224 is advanced through the introducer sheath 220 until the inflatable connection rod 222 advances between the two portals and the proximal end of the inflatable connection rod 222 lies cranial to the portal on the bone screw 208 in the cranial-ward vertebrae 212 while the distal end of the inflatable connection rod 222 lies caudal to the portal on the bone screw 208 in the caudal-ward vertebrae 200. The sheath 220 is removed and the placement is confirmed by fluoroscopy.

Figure 19:
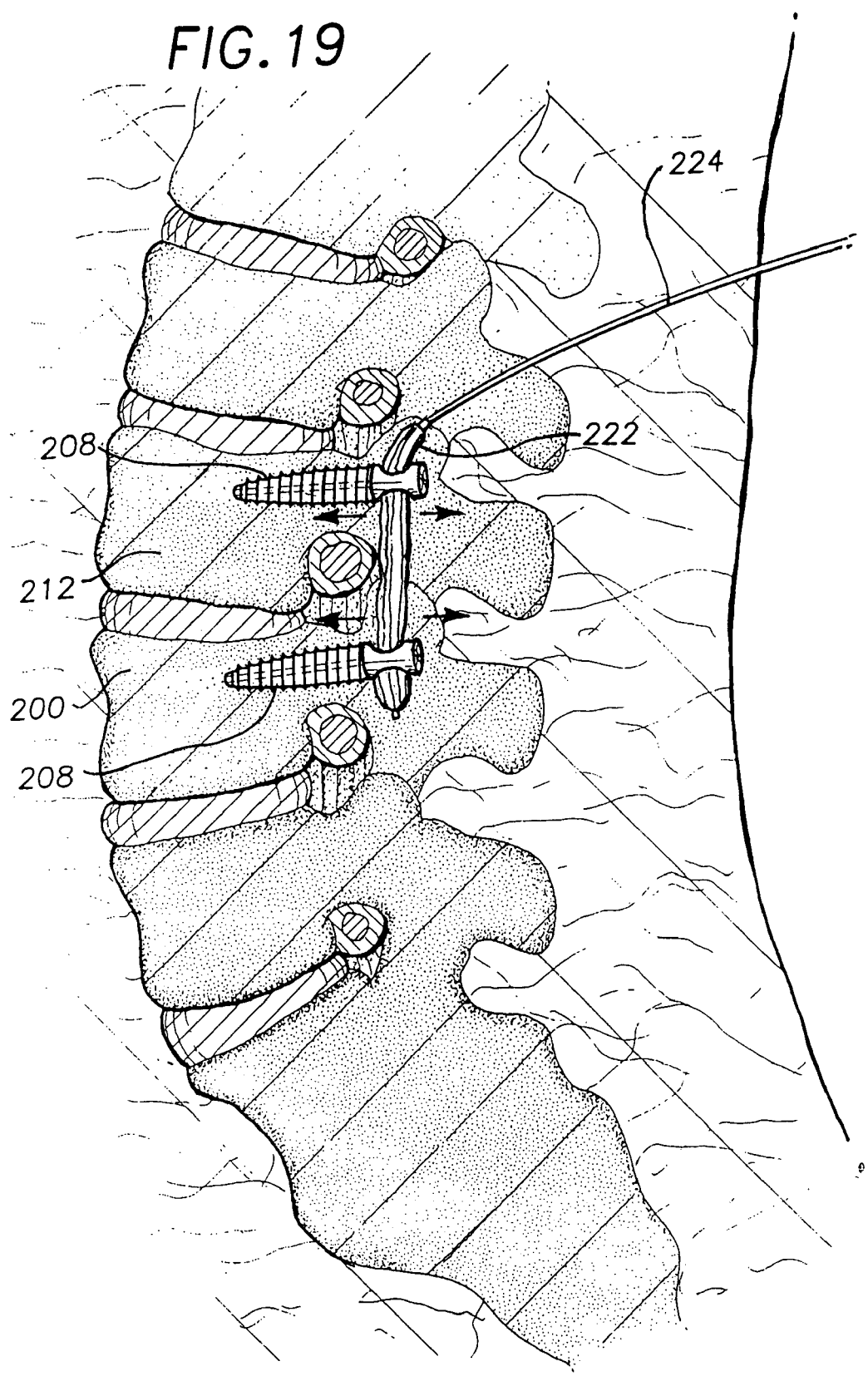

Then, as shown in FIG. 19, the balloon of the inflatable connection rod 222 is inflated with a rapid setting, liquid polymer, or its equivalent, and the polymer is allowed to set fixing each bone screw 208 in relation to each other and repositioning and fixing the vertebra 200 or portion of the vertebra that was unstable, separated or displaced. In a preferred embodiment, the liquid polymer is polymethylmethacrylate. The rapid setting, liquid polymer can comprise a light activated polymer and the method can comprise applying light to promote setting of the polymer. The inflated balloon of the inflatable connection rod 222 expands radially beyond the diameter of the portals of each bone screw 208 which helps fix the bone screws 208 in relation to each other.

Figure 20:
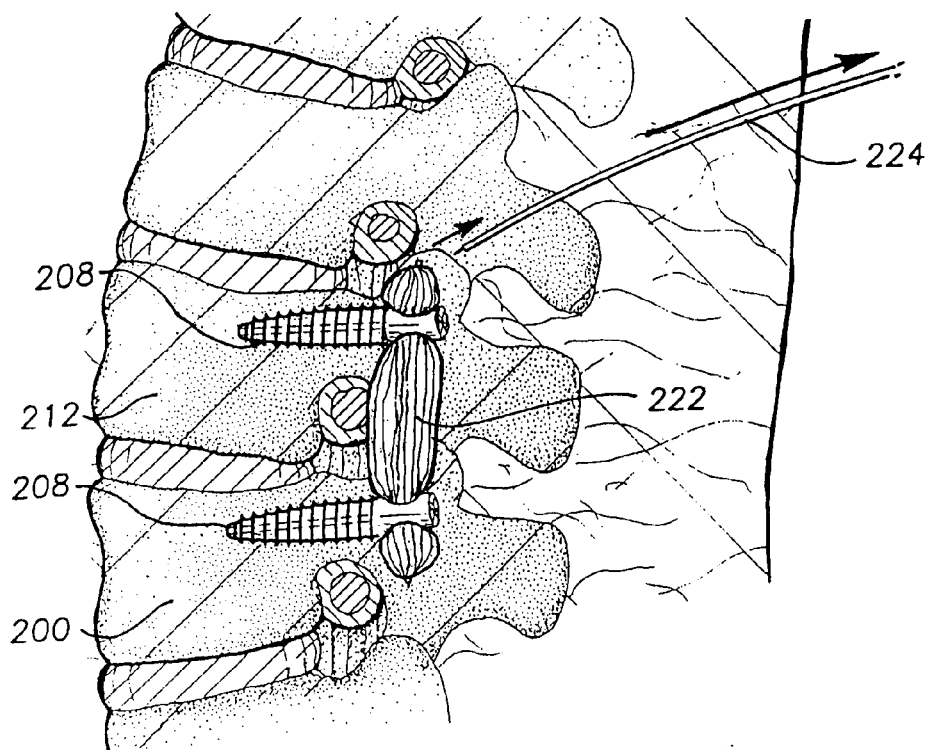

Finally, as shown in FIG. 20, the pushing catheter 224 is detached from the inflatable connection rod 222 by pulling on the pushing catheter 224 while holding the inflatable connection rod 222 to disengage the inflatable connection rod 222 from the pushing catheter 224 and the pushing catheter 224 is removed. The inflatable connection rod 222 comprises a self-sealing valve which prevents the polymer from leaking once the pushing catheter is detached. The vertebra is then fixed unilaterally. The method can be repeated on the opposite side of the spinous processes of the patient's vertebrae column, thereby repositioning or fixing the one or more unstable, separated or displaced vertebrae or the one or more portions of one or more vertebrae bilaterally. The stab incisions are closed or sealed as necessary and routine postoperative care administered.

Figure 21:
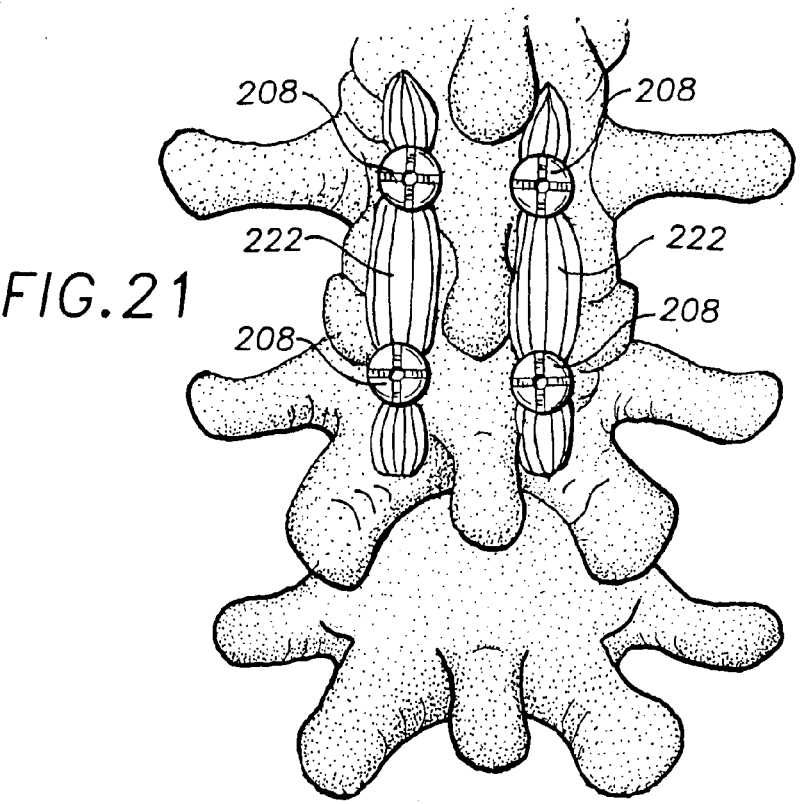
FIG. 21 shows a posterior perspective view of a portion of a vertebral column which has had some vertebrae repositioned and fixed bilaterally according to the method of the present invention.

Referring now to FIG. 21, there is shown a posterior perspective view of a portion of a vertebral column which has had some vertebrae repositioned and fixed bilaterally according to a preferred embodiment of the method of the present invention. When bilateral fixation is accomplished, it is preferred to place all bone screws before connecting the portals with inflatable connection rods.

Figure 22:
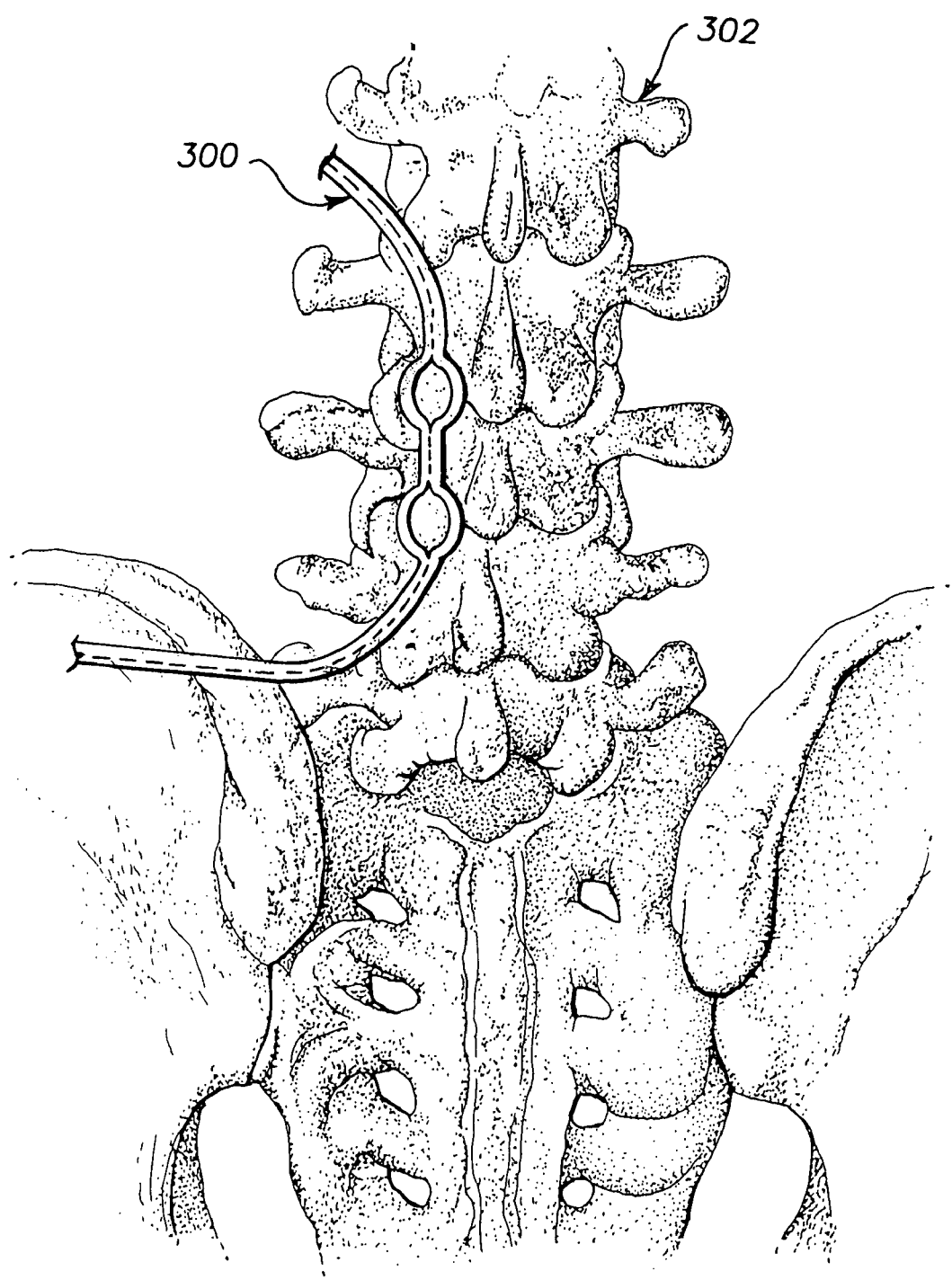
FIG. 22 through FIG. 24 show a posterior perspective view of a portion of a vertebral column undergoing the method of the present invention using a directing sheath according to the present invention.
Figure 23:
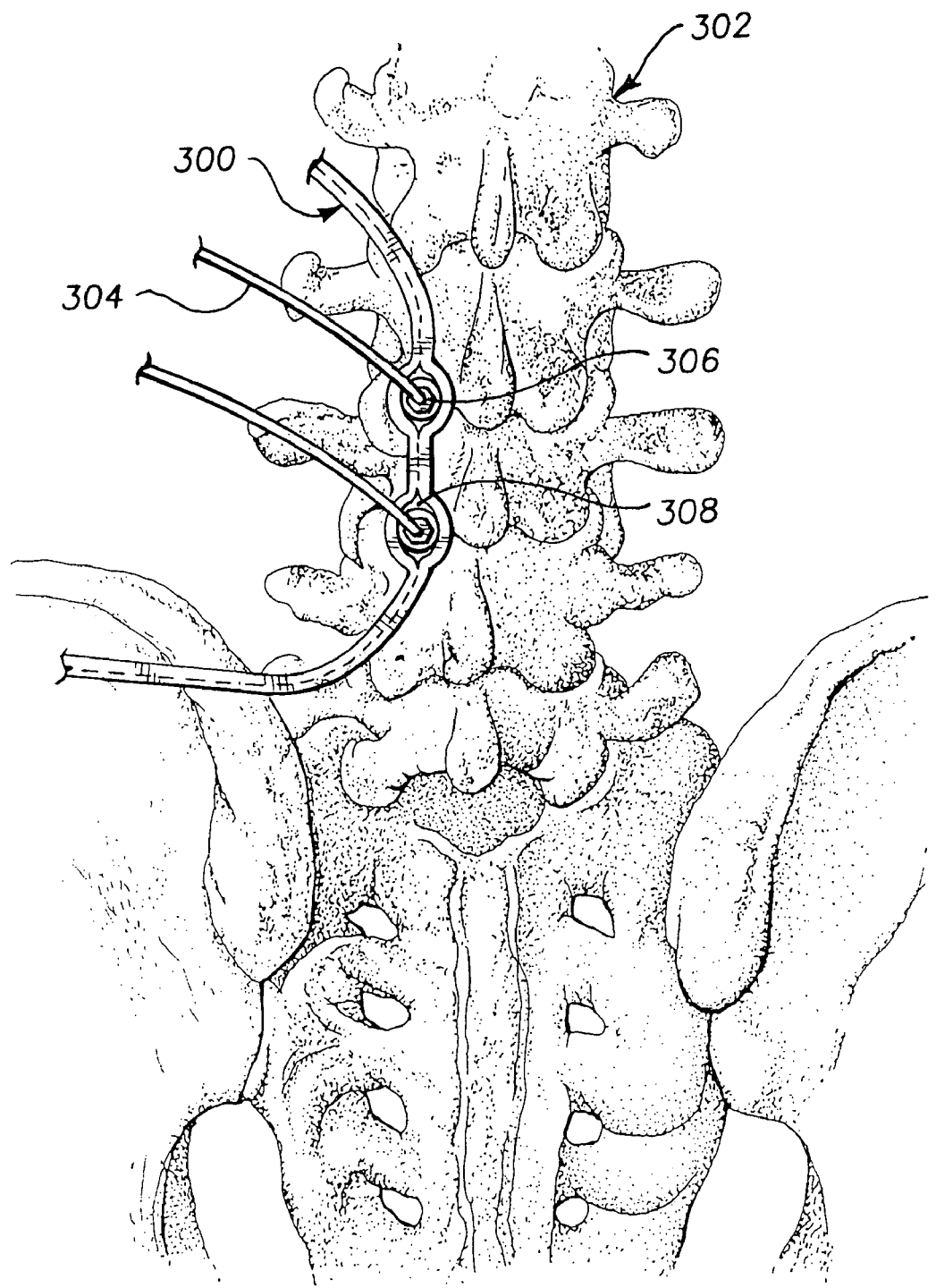
Figure 24:
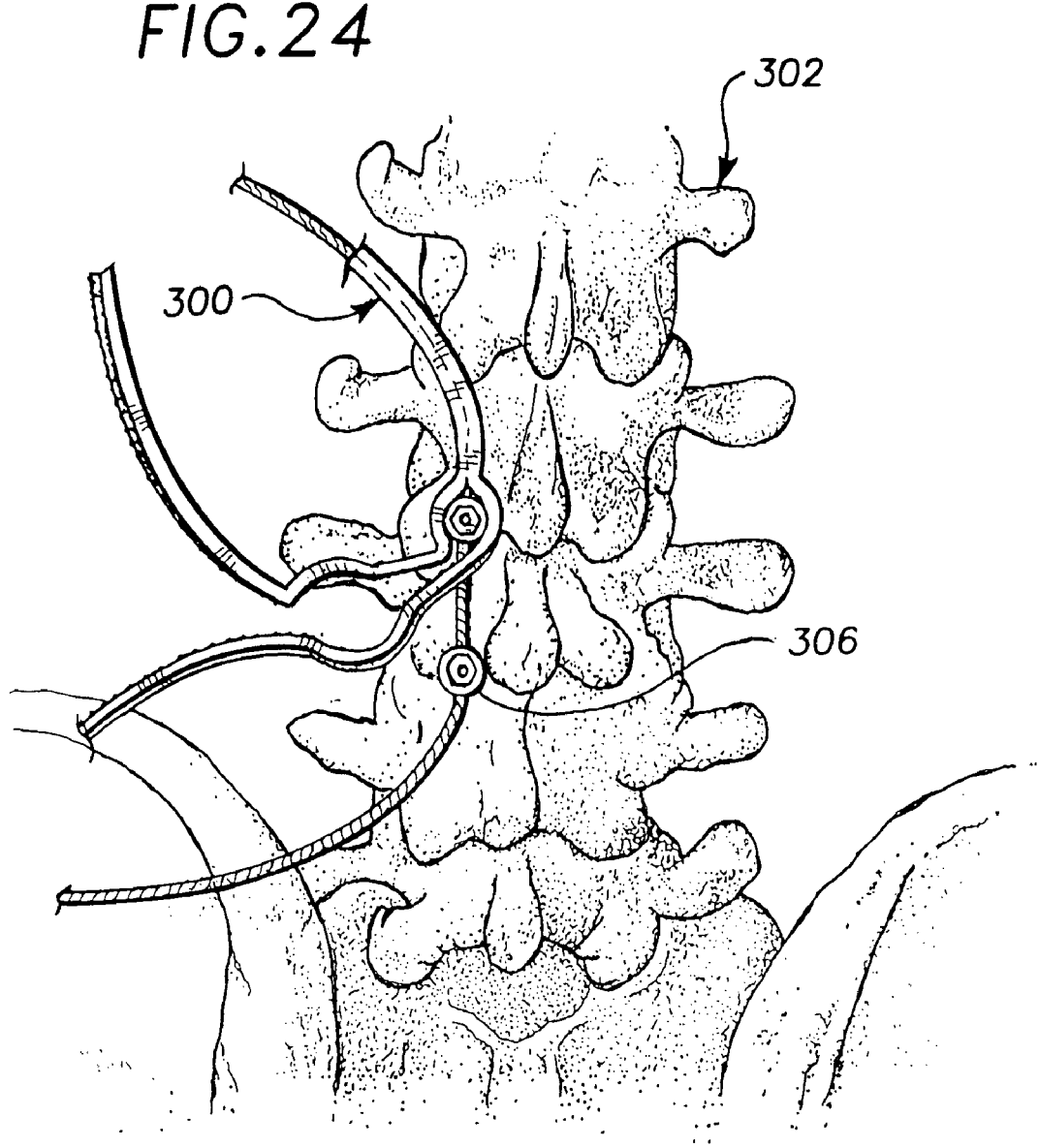

In another embodiment of the present method, a directing sheath 226 according to the present invention is advanced over a guidewire until the openings in the directing sheath 226 overlie the position in each vertebra which will receive a bone screw 208. The bone screws 208 are then placed as disclosed in this disclosure, but through the openings in the directing sheath 226, which aligns the lumen in the directing sheath with the portals of the bone screw 208. Then (not shown), a guidewire is then inserted into the lumen of the directing sheath at the proximal end of the directing sheath and advanced until the guidewire passes through each portal of the bone screws and exits the body through the lumen of the directing sheath at the distal end. The directing sheath is then removed by peeling the sheath apart along the scored lines and pulling the two halves out from the body. The guidewire that was in the lumen of the directing sheath remains in place to guide the placement of the uninflated, inflatable connection rod. Alternately, the uninflated, inflatable connection rod can be inserted directly into the lumen of the directing sheath at the proximal end and advanced until the uninflated, inflatable connection rod is properly positioned between the portals of the bone screws. Referring now to FIG. 22 through FIG. 24, there are shown posterior perspective views of a portion of a vertebral column undergoing the method of the present invention using a directing sheath according to the present invention, showing the bone screws placed through the openings of the directing sheath. As can be seen in, FIG. 22, the directing sheath 300 is positioned adjacent the vertebral column 302 according to the present invention. Next as can be seen in FIG. 23, guidewires 304 are used to place bone screws 306 through openings 308 in the directing sheath 300. Finally as can be seen in FIG. 24, the directing sheath 300 is removed by the directing sheath 300 into two separate halves.

In a preferred embodiment, there is provided a kit for performing the method of the present invention. The kit comprises a plurality of bone screws according to the present invention. The kit can also comprise other components of the system of the present invention, such as a guidewire directing device, an inflatable connection rod and a directing sheath. In another preferred embodiment, the kit also comprises a screwdriver according to the present invention.

Although the present invention has been discussed in considerable detail with reference to certain preferred embodiments, other embodiments are possible. Therefore, the scope of the appended claims should not be limited to the description of preferred embodiments contained in this disclosure.

I claim:

1. A surgical system, comprising:
 a first bone screw comprising a proximal portion and a distal portion, the proximal portion including a head and the distal portion including a distal tip; and
 an inflatable connection rod, comprising:
 a proximal end comprising a self-sealing valve;
 a distal end comprising a tip;
 a compliant, inflatable balloon between the proximal end and the distal end; and
 a hardenable media for inflating the inflatable balloon;
 wherein, when said hardenable media is hardened, the inflatable connection rod extends through the portal of the first bone screw to form a rigid structure.

2. The surgical system of claim 1, where the balloon comprises thin, reinforcing wires.

3. The surgical system of claim 1, wherein when the hardenable media hardens, the connection rod is sufficiently rigid to fix an unstable vertebra to a stable vertebra.

4. The surgical system of claim 1, wherein the hardenable media comprises a rapid setting liquid polymer.

5. The surgical system of claim 4, wherein the rapid setting liquid polymer is light activated.

6. The surgical system of claim 1, wherein the tip is metallic.

7. The surgical system of claim 1, wherein the inflatable balloon comprises a braided polymer.

8. The surgical system of claim 1, further comprising a second bone screw comprising a proximal portion and a distal portion, the proximal portion including a head and a portal, the distal portion including a distal tip.

* * * * *